United States Patent [19]

Stice et al.

[11] Patent Number: 4,926,860

[45] Date of Patent: May 22, 1990

[54] ARTHROSCOPIC INSTRUMENTATION AND METHOD

[75] Inventors: James D. Stice, Minneapolis; Chester E. Sievert, Jr., St. Paul; Steven C. Christian, Crystal, all of Minn.

[73] Assignee: Flexmedics Corporation, Minneapolis, Minn.

[21] Appl. No.: 152,652

[22] Filed: Feb. 5, 1988

[51] Int. Cl.$^5$ .................... A61B 17/06; A61M 25/00
[52] U.S. Cl. .................... 606/144; 604/281; 604/264; 606/213; 606/224
[58] Field of Search ............ 604/264, 281, 272; 128/340, 346, 334 R, 339

[56] References Cited

U.S. PATENT DOCUMENTS

| | | | |
|---|---|---|---|
| 3,419,010 | 12/1968 | Williamson | 604/281 |
| 4,493,323 | 1/1985 | Albright | 128/340 |
| 4,518,383 | 5/1985 | Evans | 604/272 |
| 4,553,543 | 11/1985 | Amarasinghe | 128/334 |
| 4,555,243 | 11/1985 | Markham | 604/272 |
| 4,597,390 | 7/1986 | Mulhollan | 128/340 |
| 4,602,635 | 7/1986 | Mulhollan | 128/334 |
| 4,616,656 | 10/1986 | Nicholson | 128/630 |
| 4,621,640 | 11/1986 | Mulhollan | 128/340 |
| 4,665,906 | 5/1987 | Jervis | 128/92 |
| 4,702,260 | 10/1987 | Wang | 604/272 |
| 4,776,844 | 10/1988 | Ueda | 604/281 |

OTHER PUBLICATIONS

Concept Zone Specific Cannula Set (promotional brochure); (15.1).
Steven Ashley, "Metals That Remember", Popular Science, pp. 78–81, 115 (Jan. 1988).

*Primary Examiner*—Edward M. Coven
*Assistant Examiner*—Gary Jackson
*Attorney, Agent, or Firm*—James R. Haller; Gregory P. Kaihoi; Mary P. Bauman

[57] ABSTRACT

Arthroscopic instrumentation for use in arthroscopic surgery and similar procedures. The instrumentation includes a cannula having a curved lumen and an elongated, flexible normally straight shape memory alloy probe. The probe is insertable into the lumen of the cannula, which in turn can be directed to a hard to reach operative site. The cannula causes the probe to bend as it passes the curves of the cannula, but the shape memory character of the probe causes the probe to exit the distal end of the cannula in a substantially straight orientation.

19 Claims, 6 Drawing Sheets

ARTHROSCOPIC INSTRUMENTATION AND METHOD

The invention relates to arthroscopic instrumentation and methods employing such instrumentation, and more particularly to the use of shape memory alloys in such instrumentation and methods.

BACKGROUND OF THE INVENTION

Arthroscopic procedures are becoming an increasingly popular approach for less-invasive orthopedic diagnosis and therapy. As clinical experience is gained, more advanced procedures have become feasible, demanding more sophisticated and higher performance instrumentation and methods. A significant limitation on arthroscopic procedures is the lack of accessibility to specific joint spaces, for example, in the knee.

Curved guiding cannulas have been developed to assist in delivery of flexible probes such as needles to tissue otherwise unreachable to the arthroscopist without significant tissue trauma. Such cannulas are typically rigid, hollow, tubular devices usually constructed of stainless steel or plastic. These devices can be provided with special features such as finger grips or ports at the proximal end to facilitate manual control and/or fluid introduction and removal. The shafts are generally rigid to prevent collapse during use and to facilitate introduction of the cannula into the tissue. Rigidity also generally is required to adequately constrain and guide accessories passed through the cannula. The distal end usually is tapered radially inwardly to ease the insertion process.

Although probes may be used without such access cannulas, there are several distinct advantages to cannula use. First, once positioned, a cannula provides repeated access to the operative location without repeated puncturing of tissue. Second, some probes are not sufficiently rigid or controllable to assure proper navigation about anatomical variances without the use of a cannula. Finally, some probes have trauma producing features (e.g., cutting edges, rasps) which prohibit their insertion into tissue without the protection of a cannula.

Precisely curved cannulas theoretically may be capable of permitting access to remote areas of a joint such as a knee, but probes must be capable of navigating such curved passageways without being damaged themselves. For example, stainless steel needles used to suture tears in the meniscus of a knee are capable of navigating only relatively gentle curves without emerging from the distal end of a cannula with a permanent bend or set.

SUMMARY OF THE INVENTION

The invention provides arthroscopic instrumentation for providing access to a remote operative location. The instrumentation comprises a cannula having a curved lumen with an end thereof being directable to an operative location, and an elongated, flexible, normally straight shape memory alloy (SMA) probe receivable in the cannula for introduction to the operative location. The cannula is configured and arranged to cause the initially straight probe to bend during its passage through the curved lumen of the cannula, but to exit from the end of the cannula in its initially substantially straight orientation.

In a preferred embodiment, the probe comprises a needle used to suture torn tissue such as the meniscus of the knee. The needle includes a sharp distal end, and pulls a suture from its proximal end. Preferably the suture is attached to the proximal end of the needle by a sheath having a first end for receiving therein the proximal end of the needle, and a second end for receiving therein a portion of the suture. In one embodiment the sheath comprises a crimpable material for compressively retaining therein the proximal end of the needle and the portion of the suture.

The SMA needle is able to bend along the path of the cannula and emerge in a substantially straight configuration, greatly facilitating accurate repair of torn tissue. Nitinol is a preferred SMA. In a particularly preferred embodiment, a pair of such needles are attached at their proximal ends to opposite ends of a suture. In use, a curved cannula is inserted into the body with the distal end of the cannula adjacent the operative location. One of the needles is then inserted into the lumen of the cannula from the proximal end thereof and advanced through the lumen so that the needle undergoes a bend as it passes therethrough but without taking on a substantial set. The distal end of the needle is forced through the distal end of the cannula and emerges in a substantially straight orientation as it advances toward the operative location. The needle is then advanced through the appropriate tissue, exiting out the other side. The second needle is then passed through the cannula in like fashion, exiting the tissue on the other side. The needles are then separated from the suture, and the suture is snugged up and tied off to hold the tissue together.

Due to the relative expense of many SMA's, including nitinol, compared to other materials such as stainless steel, it is desirable to attach the suture to the needles in a fashion that permits re-use of the needles, but without substantially increasing the diameter of the needles so as to prevent undue tissue trauma as the needle passes through. Thus, in a preferred embodiment, the connecting sheath is disconnectable to permit the needle to be reconnected to another suture for re-use. Such a sheath may comprise a pair of interlockable coils each having a first and a second end. The first coil is attached at its first end to the proximal end of the needle and the second coil is attached at its first end to a suture, the second ends of the coils being removably interlockable. Alternately, the sheath may comprise complimentary interlockable bayonet portions respectively attached to the proximal end of the needle and the suture.

In another embodiment, the probe comprises an elongated, flexible shaft for delivery of a dart used to secure torn tissue, the dart thus being utilized in lieu of sutures. The shaft includes suitable means at its distal end to carry and release the dart upon insertion of it in the proper location in the tissue.

To facilitate manipulation of a probe, the invention also provides a removable handle for gripping slender, flexible probes such as needles. Preferably the handle comprises a body having an elongated bore and an elongated slot intersecting the bore to enable a probe to be placed in and removed from the bore, and includes releasable gripping means for gripping a probe placed in the bore. In a preferred embodiment, the gripping means comprises a cammed lever extending outwardly through an aperture in the body, the lever being pivotable between a first position freely allowing insertion of the probe and a second locking position preventing substantial rotational or longitudinal movement of the probe. In another embodiment, the gripping means comprises a plurality of radially compressable portions carried by the body and compression collar means for compressing the compressable portions against the probe to prevent substantial rotational or longitudinal movement of the probe. The outwardly accessible longitudinal slot of the handle is particularly useful when the handle is used to grip needles connected by a suture. Such needles are typically used to suture tissue in a procedure requiring that both needles pass through the cannula. After the first needle is inserted, the handle of the invention may be removed from and placed on the other needle, and after insertion of the second needle the handle may be removed altogether. Without the longitudinal slot, the handle would not be removable from the second needle without cutting the suture, a counterproductive option.

BRIEF DESCRIPTION OF THE DRAWINGS

FIG. 9 is a cross-sectional view of yet another alternative handle; an

BEST MODE FOR CARRYING OUT THE INVENTION

Figure 1:
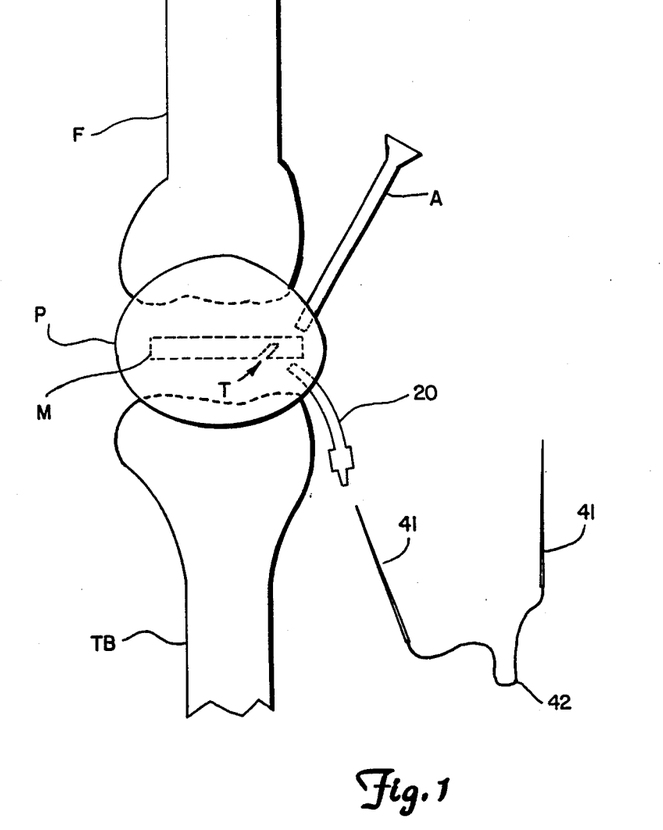
FIG. 1 is a schematic representation of an arthroscope and curved cannula inserted into a knee undergoing arthroscopic surgery.

Referring to FIG. 1, a method of arthroscopic surgery is illustrated. An arthroscope (A) is inserted into a first location providing visual access to the tissue to be repaired, such as the meniscus (M) of a knee which has a tear (T) in it. The joint is represented somewhat schematically by the lower end of the Femur (F), the upper end of the tibia (TB) and the patella (P). A variety of tools may be used to cut, abrade, measure, pierce, move or otherwise manipulate tissue. To deliver these tools to the appropriate location without unnecessary tissue trauma, a cannula 20 is inserted from another location and advanced to a point adjacent the tissue to be manipulated. The cannula 20 typically includes one or more bends to permit delivery of the probe to a location and in an orientation not otherwise possible. Upon proper placement of the cannula 20, the probe is inserted and the selected procedure performed.

In the case illustrated, the probe comprises a pair of two needles 41 connected to opposite ends of a suture 42. The first of the needles is inserted into the proximal end of the cannula 20 and advanced so that the distal end of the needle exits the distal end of the cannula 20. Typically the needles are about ten inches in length, sufficient to extend beyond both ends of the cannula and through the tissue being repaired. The needle 41 exits the distal end in a substantially straight configuration, and therefore may be accurately advanced to, into, and through the meniscal tissue (M), exiting the other side. The other needle is then similarly inserted into the cannula and advanced through the tissue at a location adjacent the passage of the first needle. When both needles have exited the other side, the needles are separated from the suture, and the suture is tied off.

In another method of repairing such torn tissue, a dart is utilized in lieu of sutures. Typically such darts are biodegradable, surgical barbed structures shaped to forwardly pierce tissue, the barbs acting to restrain rearward withdrawal once inserted. Such darts have the advantage of not requiring that the needle/suture entirely pierce the tissue and pass out the other side of the knee (or other area being repaired). Rather, access to only one side of the tissue is required. Insertion of the dart causes the torn tissue to be held together in a configuration suitable for healing, and the barbs prevent the tissue from separating during the healing process.

In an embodiment of the invention utilizing such darts, the probe comprises a flexible, elongated shaft having means at its distal end to carry and release the dart upon insertion of it in the proper location in the tissue. The distal end of the shaft may be merely blunt, fitting snugly within a receptive cavity in the proximal end of the dart. Other suitable configurations may also be devised, requiring merely that the distal end of the shaft be able to advance the dart to the proper location.

The distal end of a probe of the invention may be changeable to facilitate use of a variety of tools or have a single tool with a single shaft. For example, the distal end of a SMA shaft may be permanently fitted with a stainless steel (or other suitable material) tool or a tip bearing threads or helical coil on the distal end thereof. Tools of varying configurations having complimentary threads or a helical coil may then be interchangeably attached to the shaft.

A number of shape memory alloys are known to exhibit the superelastic/pseudoelastic shape recovery characteristic of probes of the invention. Such alloys generally are characterized by their ability, at room/body temperature, to be deformed from an austenitic crystal structure to a stress-induced martensitic structure, returning to the austenitic state when the stress is removed. The alternate crystal structures give the alloy superelastic or pseudoelastic properties. Alternatively, a cold worked martensitic microstructure can be used to give enhanced shape recovery and a lower stiffness than stainless steel. Nitinol, an alloy of nickel and titanium, is a particularly preferred alloy in that it is commercially available and has been studied somewhat more than many other SMA's.

Figure 2:
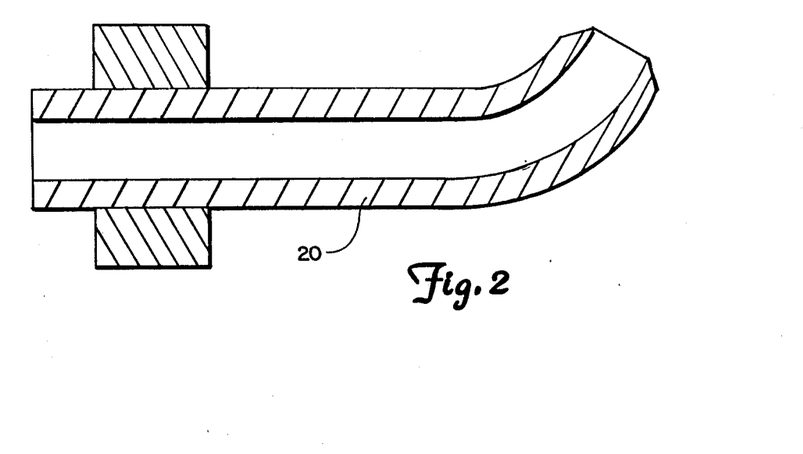
FIG. 2 is a cross-sectional view of a curved cannula.
Figure 6:
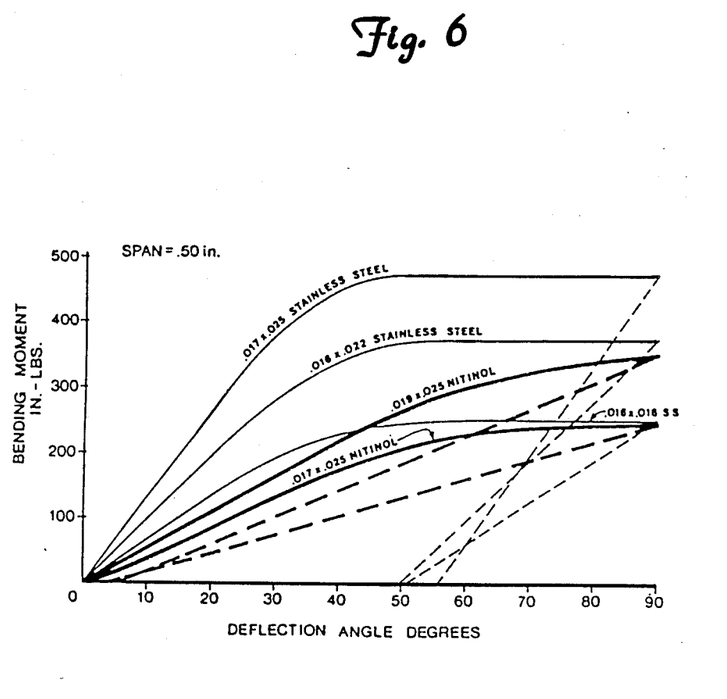
FIG. 6 is a graph depicting bending moment versus deflection angle of various sizes of stainless steel and nitinol.

FIG. 2 depicts one of a variety of curved configurations for the cannula 20. Although nitinol is substantially more flexible and exhibits much greater shape recovery for a similar deformation than stainless steel and similar materials, even it will take a slight set if the curve in the cannula is too severe. FIG. 6 depicts the bending moment of stainless steel and nitinol of various diameters against deflection angle. From the graph it can be seen that, even though bent through a substantial angle, when unloaded the nitinol returns to a near-zero deflection, whereas comparable stainless steel takes a substantial permanent set. The graph also illustrates nitinol's relatively flexible nature, in that substantially less force is required to deflect it than is required to deflect stainless steel to a comparable angle. Thus, a nitinol needle will advance around curves in a cannula with much less effort than a comparable size stainless steel needle. It also emerges from the cannula curves substantially straight; that is, with little or no permanent bend or set.

Figure 3:
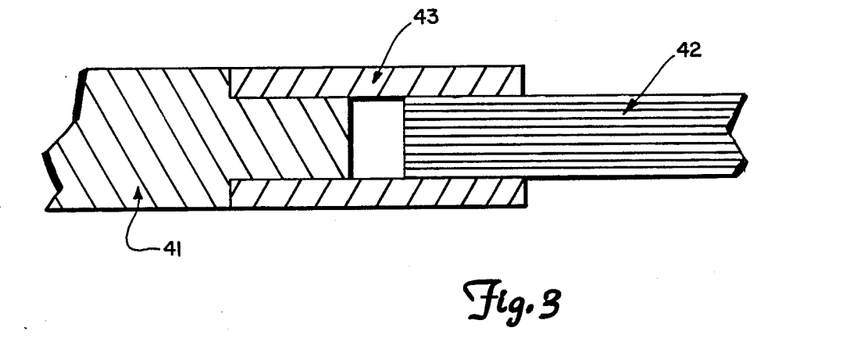
FIG. 3 is a cross-sectional, broken-away view of a needle connected to a suture by a sheath.

FIG. 3 depicts a method of connecting a suture 42 to a disposable SMA needle 41. A crimpable sheath 43 of an outer diameter approximately equal to the needle 41 receives within its hollow core an end portion of the needle 41 which has been ground to a reduced outer diameter. An end of the suture 42 is inserted into the other end of the sheath 43, and the sheath is then crimped to frictionally retain both elements therein. The crimpable sheath 43 may be of any suitable material, but desirably is of stainless steel.

Most SMA's including nitinol presently are relatively more expensive than materials such as stainless steel, and therefore it is desirable to provide for detachable reattachment of sutures to the needles, permitting their re-use. Traditional eyelets in the proximal end of the needles are undesirable because they require the suture to pass through the needle at a right angle to the longitudinal dimension of the needle. thereby presenting a broader profile to the tissue and consequently causing undesirable tissue trauma. The invention therefore provides a detachable sheath. In one embodiment, the sheath comprises two parts. One of the parts is permanently connected to the proximal end of a needle 41, and the other part is connected to an end of the suture 42. The parts then may be attached for use in the above described procedure, and the needles may be detached from the suture after such use, thereby permitting their sterilization and reattachment to a fresh suture for re-use.

Figure 4:
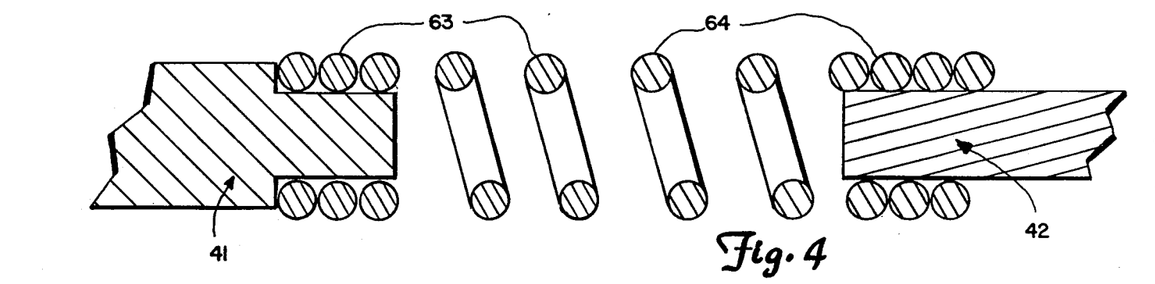
FIG. 4 is a cross-sectional, broken-away view of a needle connectable to a suture by a disconnectable, helical sheath.

In one embodiment, shown in FIG. 4, the sheath comprises a pair of coils 63 and 64 respectively attached to the needle 41 and suture 42. The coils may be so attached by any suitable means, including by compression and/or use of suitable adhesives. In a preferred method of assembly, the coil is either torqued open or the coil is spun about its axis, and the end of the suture or needle is inserted into the thus broadened diameter of the coil. The needle 41 and suture 42 do not extend entirely through the coils 63 and 64, but only a portion of the way. The remaining portion of the coils are sized to thread together, forming a secure connection between them for use in the operative procedure. If the spacing between adjacent winds of the coils is slightly smaller than the diameter of the wire, an extra-snug fit is obtained.

Figure 5:
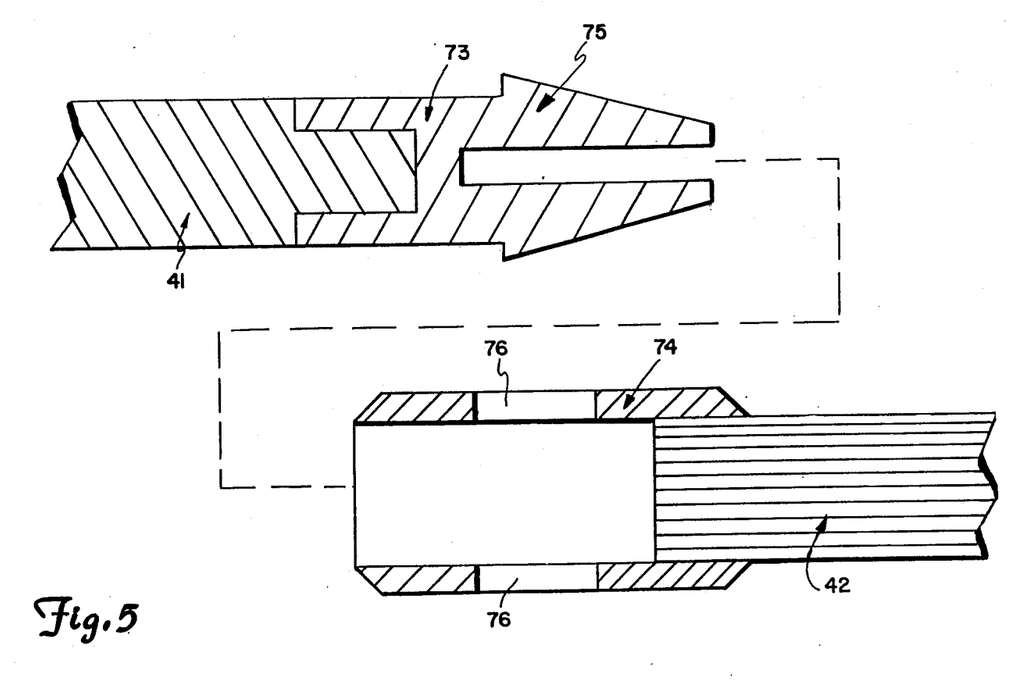
FIG. 5 is an exploded cross-sectional view of a bayonet-type sheath.

In another embodiment, shown in FIG. 5, the disconnectable sheath constitutes a pair of pieces which fit together in bayonet fashion. Body 73 is either formed integrally as a part of the needle shaft or is appropriately attached to the needle shaft, and contains a proximal portion extending therefrom with radially protruding barbs 75. Tubular member 74 is affixed to an end of the suture 42, and includes therein complimentary slots 76 for receiving therein the barbs 75. Under surgical conditions, the bayonet joint is strong enough to withstand separation, but manual depression of the barbs 75 permits detachment of the pieces from one another for re-use of the needle.

In yet another embodiment, which is also depicted by FIG. 3, the sheath comprises a one piece sheath constructed of a suitable SMA. The sheath is formed to have a lower yield stress with, in some instances, a larger diameter at one temperature (e.g., in a martensitic state at a relatively low temperature), and a higher yield stress with a smaller diameter at another temperature (e.g., in its austenitic state at room temperature). When the sheath is cooled, the needle end and suture may be inserted. As the sheath warms to room temperature, the sheath contracts, forming a secure compression joint. Ridges may be provided on the respective parts to enhance the engagement, if desired.

Many types of probes include handles of varying configurations near their proximal ends to facilitate manipulation. Such handles are particularly useful on probes subject to forces that might buckle the probe shaft, or on very small diameter probes that must be rotated or otherwise manipulated in a precise manner. For probes that are meant to be passed through the cannula entirely such as needles, however, such handles may not be permanently attached to the probe, lest they prevent insertion of the probe through the cannula.

Figure 7:
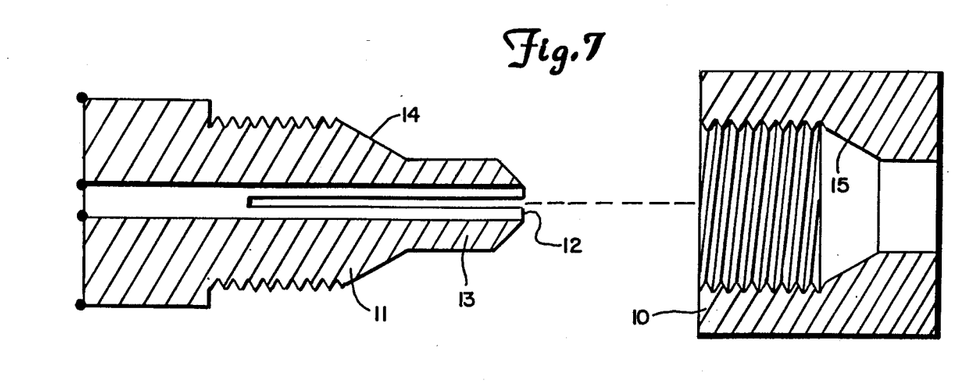
FIG. 7 is an exploded, cross-sectional view of a probe handle of the invention.
Figure 8:
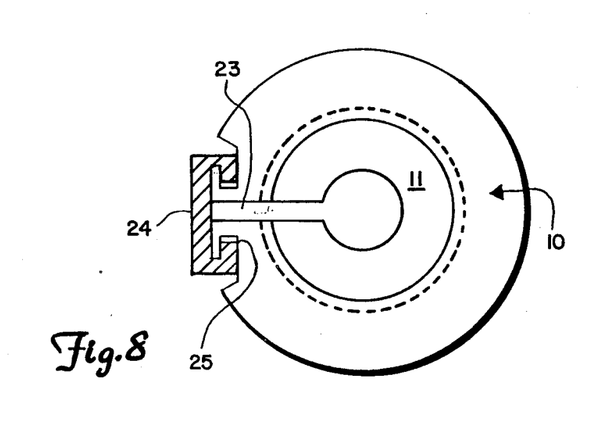
FIG. 8 is an end view of the probe handle of FIG. 7.
Figure 8A:
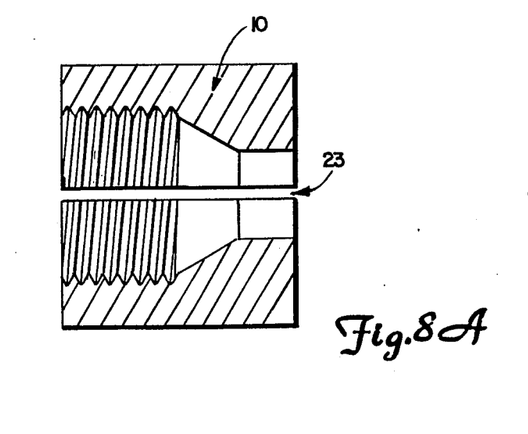
FIG. 8A is a cross-sectional view of the handle body FIG. 8.

FIG. 7 depicts a removable handle usable with such probes. The handle includes a body 11 having male threads thereon, and a compression collar 10 having female threads therein. Axially extending slots 12 in the body form a plurality of radially compressable elements 13 carried by the body, the elements being resiliently radially compressable in response to interaction of camming surfaces 14 and 15 of the body and collar respectively as the collar is threaded onto the body. Probes such as needles that are passed entirely through the cannula typically are used in pairs attached by a suture. FIG. 8 depicts a longitudinal slot 23 intersecting the bore of the body 11 and the collar 10 to permit a probe (or suture) to be removed from or inserted into the handle. The compression collar 10 includes means receiving a latch 24 which resists tensile forces which would spread the slot 23 as the collar is tighened onto the body 11. In the embodiment illustrated, the latch 24 comprises a longitudinal C-channel slidingly receivable in a complimentary track 25 in the collar 20. Other types of latches may also be utilized to resist such spreading/tensile forces.

Figure 9:
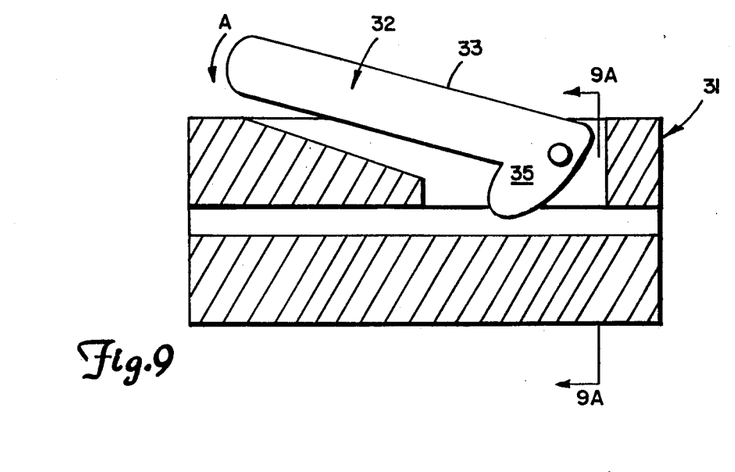
Figure 9A:
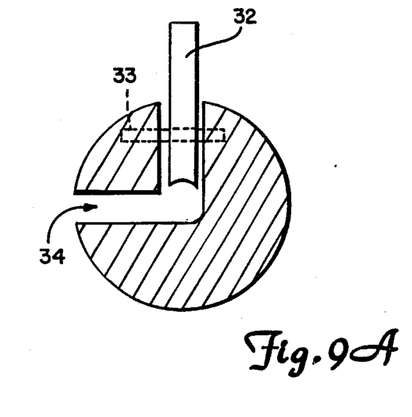
FIG. 9A is a cross-sectional view of FIG. 9 taken along line 9A—9A thereof.

In a preferred embodiment, the removable handle is comprised of a body portion 31 having a bore and a radially extending longitudinal slot 34 for receiving the probe or suture. A pivoting camming lever 32 is provided with a handle portion 33 and a nose portion 35 angled with respect to the handle portion so as to come into contact with a probe in the bore when the handle is pivoted in the direction shown by the arrow "A." The lever 32 may be secured in the locked/engaged position shown in FIG. 9 by finger pressure. The slot 34 is not necessary for some applications where the handle may be slid onto the probe from the proximal end.

In use, a removable handle is secured to the proximal portion of a needle or other similar probe. The needle is then inserted into the cannula. The handle may then be removed or merely slid off the end of the needle, along the suture, and onto the proximal portion of the other needle where it is secured. The second needle is then inserted into the cannula, and the handle may then be removed to allow the suture to be drawn entirely through the cannula and into the operative location.

Although the invention has been described with specific reference to needles and arthroscopic suturing of the meniscus of the knee, other types of SMA probes may be utilized in such surgical techniques with similar benefit. Probe ends may be fashioned into tools for such functions as puncturing, cutting, pulling or pushing, rasping, measuring or cauterizing tissue. Furthermore, SMA needles may be utilized in other techniques requiring remote delivery of such a needle through a tortuous path.

While a preferred embodiment of the present invention has been described, it should be understood that various changes, adaptations and modifications may be made without departing from the spirit of the invention and the scope of the appended claims.

What is claimed is:

1. Arthroscopic instrumentation comprising a cannula having a curved lumen, an end thereof being directable to an operative location; and an elongated, flexible, normally straight shape memory alloy probe receivable in the cannula for introduction to the operative location, the cannula being configured to cause the probe to bend during its passage through the curved lumen, the shape memory character of the probe causing the probe to exit from the end of the cannula in a substantially straight orientation.

2. The instrumentation of claim 1 wherein the probe comprises a nitinol needle having a sharp distal end.

3. The instrumentation of claim 2 wherein the needle is longer than the cannula, thereby permitting the needle to be manually inserted in one end of the cannula and manually withdrawn from the other end.

4. The instrumentation of claim 2 including a suture, and connector means for connecting one end of the the suture to a proximal end of the needle.

5. The instrumentation of claim 4 including a second such needle, and connector means for connecting the other end of the suture to a proximal end of the second needle.

6. The instrumentation of claim 4 wherein the connector means comprises a sheath having a first end for receiving therein the proximal end of the needle, and a second end for receiving therein a portion of the suture.

7. The instrumentation of claim 6 wherein the sheath is comprised of a crimpable material for compressively retaining therein the proximal end of the needle and the portion of the suture.

8. The instrumentation of claim 6 wherein the proximal end of the needle is of a smaller diameter than the adjacent portion of the needle, and the sheath has an outer diameter approximately the same as said adjacent portion of the needle.

9. The instrumentation of claim 6 wherein the sheath is disconnectable to permit the needle to be reconnected to another suture for re-use.

10. The instrumentation of claim 9 wherein the sheath comprises a pair of interlockable coils each having a first and a second end, the first coil being attached at its first end to the proximal end of the needle and the second coil being attached at its first end to a suture, the second ends of the coils being removably interlockable.

11. The instrumentation of claim 9 wherein the sheath comprises complimentary interlockable bayonet portions respectively attached to the proximal end of the needle and the suture.

12. The instrumentation of claim 9 wherein the sheath is comprised of a shape memory alloy having a lower yield stress at one temperature and a smaller diameter and higher yield stress at room/body temperature.

13. Arthroscopic instrumentation comprising:
a cannula having a curved lumen, an end thereof being directable to an operative location; and
a pair of elongated, flexible, normally straight nitinol needles receivable in the cannula for introduction to the operative location, the needles being longer than the cannula thereby permitting them to be manually inserted in one end of the cannula and manually withdrawn from the other end;
a suture, and connector means associated with each needle for connecting the suture to a proximal end of that needle, the connector means comprising a sheath having complimentary interlockable portions respectively attached to the proximal end of the needle and the suture, the portions being disconnectable to permit the needles to be reconnected to another suture for re-use;
the proximal end portion of each needle being of a smaller diameter than the adjacent portion of the needle, and the sheath having an outer diameter approximately the same as said adjacent portion of the needle;
the needles and cannula being configured and arranged to permit the needles to be bent as they pass through the curved lumen of the cannula but to exit in a substantially straight configuration without taking a substantial set from the bending thereof.

14. The instrumentation of claim 13 wherein the sheath comprises a pair of interlockable coils each having first and second ends, the first coil being attached at its first end to the proximal end of the needle and the second coil being attached at its first end to a suture, the second ends of the coils being removably interlockable.

15. The instrumentation of claim 13 further including a removable handle for gripping one of the needles comprising a body having an elongated bore and an elongated slot intersecting the bore to enable the needle to be placed in and removed from the bore, and releasable gripping means for gripping the needle when it is placed in the bore.

16. A method of inserting a probe into an operative location comprising the steps of:
placing the distal end of a curved cannula adjacent the operative location;
inserting a shape memory alloy probe into the lumen of the cannula from the proximal end of the cannula and advancing the probe through the lumen so that the probe undergoes a bend as it passes through the curved lumen of the cannula but without taking on a substantial set, and forcing the distal end of the probe through the distal end of the cannula from which the distal end of the probe emerges in a substantially straight orientation as it advances toward the operative location.

17. A method of arthroscopically suturing tissue comprising the steps of:
placing the distal end of a curved cannula in alignment with the tissue to be sutured;
inserting a shape memory alloy needle through the curved cannula, the needle exiting the cannula in a substantially straight orientation toward the tissue and pulling a suture behind it;
advancing the needle until it exits the tissue;
inserting a second needle through the curved cannula, the needle exiting the cannula in a substantially straight orientation toward the tissue and pulling the other end of the suture behind it;
advancing the second needle until it exits the tissue, and then separating the needles from the suture and tying off the suture.

18. A method of arthroscopically suturing tissue comprising the steps of:
  placing the distal end of a curved cannula in alignment with the tissue to be sutured;
  inserting a shape memory alloy needle through the curved cannula, the needle exiting the cannula in a substantially straight orientation toward the tissue and pulling a suture behind it;
  advancing the needle until it exits the tissue;
  inserting a second needle through the curved cannula, the needle exiting the cannula in a substantially straight orientation toward the tissue and pulling the other end of the suture behind it;
  advancing the second needle until it exits the tissue, and then separating the needles from the suture and typing off the suture; and re-attaching the needles to another suture.

19. The method of claim 18 wherein the suture is attached to each needle by a pair of separable, interlockable sheaths, the separating step comprising the step of separating the sheaths.

* * * * *